(12) United States Patent
Yanagida et al.

(10) Patent No.: US 9,463,164 B2
(45) Date of Patent: Oct. 11, 2016

(54) TABLET HAVING IMPROVED ELUTION PROPERTIES

(71) Applicant: SUMITOMO DAINIPPON PHARMA CO., LTD., Chuo-Ku, Osaka-Shi, Osaka (JP)

(72) Inventors: Makiko Yanagida, Ibaraki (JP); Hiroyuki Nishii, Ibaraki (JP); Masayuki Nakazono, Ibaraki (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 14/160,861

(22) Filed: Jan. 22, 2014

(65) Prior Publication Data

US 2014/0135352 A1    May 15, 2014

Related U.S. Application Data

(62) Division of application No. 12/866,999, filed as application No. PCT/JP2009/052231 on Feb. 10, 2009, now Pat. No. 8,673,353.

(60) Provisional application No. 61/064,012, filed on Feb. 11, 2008.

(51) Int. Cl.
*A61K 9/20* (2006.01)
*A61K 31/517* (2006.01)
*A61K 9/28* (2006.01)

(52) U.S. Cl.
CPC .......... *A61K 9/2054* (2013.01); *A61K 9/2018* (2013.01); *A61K 9/284* (2013.01); *A61K 9/2866* (2013.01); *A61K 31/517* (2013.01)

(58) Field of Classification Search
None
See application file for complete search history.

(56) References Cited

U.S. PATENT DOCUMENTS

| 5,780,632 | A  | 7/1998 | Saji et al. |
| 7,329,665 | B2 | 2/2008 | Muraoka et al. |
| 2004/0028741 | A1 | 2/2004 | Fujihara |
| 2005/0032819 | A1 | 2/2005 | Muraoka et al. |
| 2005/0142192 | A1 | 6/2005 | Benjamin et al. |
| 2009/0143404 | A1 | 6/2009 | Fujihara |

FOREIGN PATENT DOCUMENTS

| JP | 8-325146 A | 12/1996 |
| JP | 2800953 B2 | 7/1998 |
| JP | 2000-26292 A | 1/2000 |
| JP | 2006-117535 A | 5/2006 |
| JP | 2006-188466 A | 7/2006 |
| JP | 2007-509055 A | 4/2007 |
| WO | 00/29390 A1 | 5/2000 |
| WO | 02/24166 A1 | 3/2002 |
| WO | 03/016299 A1 | 2/2003 |
| WO | 2004/078173 A1 | 9/2004 |
| WO | 2006/126681 A1 | 11/2006 |
| WO | 2006/132360 A1 | 12/2006 |
| WO | 2007/148786 A1 | 12/2007 |

OTHER PUBLICATIONS

Extended European Search Report dated Jan. 31, 2013 in European Patent Application No. 09710487.1 to Dainippon Sumitomo Pharma Co., Ltd.
Handbook of Pharmaceutical Excipients, Second Edition, Edited by Ainley Wade and Paul J. Weller, American Pharmaceutical Association, Washington, The Pharmaceutical Press, London, 1994, pp. 491-493.

*Primary Examiner* — Tigabu Kassa
(74) *Attorney, Agent, or Firm* — Sughrue Mion, PLLC

(57) ABSTRACT

The present invention provides a tablet having improved dissolution property, which comprises (+)-3-{1-[3-(trifluoromethoxy)benzyl]piperidin-4-yl}-4-phenyl-3,4-dihydro-2 (1H)-quinazolinone or a pharmaceutically acceptable salt thereof as an active component, and a production method thereof. A film-coated tablet obtained by mixing granulated particles obtained by granulating a mixture containing (a) the aforementioned active component, (b) one or more kinds of fillers selected from lactose, D-mannitol, erythritol and crystalline cellulose, (c) a cellulose-based disintegrant and (d) a water-soluble binder with a later powder containing (e) one or more kinds of fillers selected from lactose, D-mannitol and crystalline cellulose and/or (f) a cellulose-based disintegrant, forming the mixture, and applying film coating. A production method of a film-coated tablet, including a step of producing the granulated particles, a step of producing a tablet by mixing with the later powder and forming the mixture, and a step of applying a film coating to the obtained tablet.

4 Claims, No Drawings

TABLET HAVING IMPROVED ELUTION PROPERTIES

CROSS REFERENCE TO RELATED APPLICATIONS

This application is a Divisional application of pending U.S. application Ser. No. 12/866,999 filed Oct. 18, 2010, which is a National Stage of International Application No. PCT/JP2009/052231 filed Feb. 10, 2009, claiming priority based on U.S. Provisional Application No. 61/064,012 filed Feb. 11, 2008, the contents of all of which are incorporated herein by reference in their entirety.

TECHNICAL FIELD

The present invention relates to a tablet having improved dissolution property (particularly, film-coated tablet), which comprises (+)-3-{1-[3-(trifluoromethoxy)benzyl]piperidin-4-yl}-4-phenyl-3,4-dihydro-2(1H)-quinazolinone (hereinafter to be referred to as compound A) or a pharmaceutically acceptable salt thereof as an active component, and a production method thereof.

BACKGROUND ART

It is known that compound A or a pharmaceutically acceptable salt thereof is useful as a therapeutic agent for frequent urination or urine incontinence and the like (patent document 1). However, a tablet having good dissolution property of compound A or a pharmaceutically acceptable salt thereof is not known.
patent document 1: WO 03/016299

DISCLOSURE OF THE INVENTION

Problems to be Solved by the Invention

The present invention provides a tablet having improved dissolution property, which comprises compound A or a pharmaceutically acceptable salt thereof as an active component, and a production method thereof.

The present inventors applied, during production steps of a tablet of compound A or a pharmaceutically acceptable salt thereof, a shading film coating to prevent decomposition by light, and found that dissolution property drastically decreases problematically. When a film coating using a water-soluble substrate is applied to general drugs, the dissolution property does not decrease much. Hence, a drastic decrease of dissolution property of compound A and a pharmaceutically acceptable salt thereof is the finding found for the first time by the present inventors, and is an unexpected problem.

Means of Solving the Problems

The present inventors have conducted intensive studies in an attempt to solve the above-mentioned problem, and unexpectedly found that a tablet obtained by mixing granulated particles obtained by granulating a mixture of the below-mentioned components (a)-(d) with the below-mentioned component (e) and/or component (f), and forming the mixture is free of decreased dissolution property even after film coating.

The present inventors have also found that a tablet comprising the below-mentioned components (a), (b'), (c) and (d), and starch, which is free of film coating, shows good dissolution property.

The present inventors have also found that a tablet having good dissolution property can be obtained by mixing granulated particles obtained by granulating a mixture of the below-mentioned components (a)-(d) with the below-mentioned component (e) and/or component (f), and forming the mixture.

The present inventors have conducted further studies based on the above-mentioned finding and completed the present invention.

Accordingly, the present invention relates to the following.

[1] A film-coated tablet obtained by mixing granulated particles obtained by granulating a mixture of (a) compound A or a pharmaceutically acceptable salt thereof, (b) one or more kinds of fillers selected from lactose, D-mannitol, erythritol and crystalline cellulose, (c) a cellulose-based disintegrant and (d) a water-soluble binder, with (e) one or more kinds of fillers selected from lactose, D-mannitol and crystalline cellulose and/or (f) a cellulose-based disintegrant, forming the mixture to give a tablet and applying film coating to the tablet (hereinafter to be also referred to as the film-coated tablet of the present invention).

[2] The film-coated tablet of the above-mentioned [1], wherein the filler of the aforementioned (b) is one or more kinds of fillers selected from lactose, D-mannitol and crystalline cellulose.

[3] The film-coated tablet of the above-mentioned [1] or [2], which is obtained by mixing granulated particles obtained by granulating a mixture of (a) compound A or a pharmaceutically acceptable salt thereof, the filler(s) of (b), (c) a cellulose-based disintegrant and (d) a water-soluble binder, with (e) one or more kinds of fillers selected from lactose, D-mannitol and crystalline cellulose and (f) a cellulose-based disintegrant, forming the mixture to give a tablet and applying film coating to the tablet.

[4] The film-coated tablet of any one of the above-mentioned [1] to [3], wherein the fillers of the aforementioned (b) and (e) are the same or different and one or more kinds selected from lactose and D-mannitol.

[5] The film-coated tablet of the above-mentioned [4], wherein the fillers of the aforementioned (b) and (e) are lactose.

[6] The film-coated tablet of any one of the above-mentioned [1] to [5], wherein the cellulose-based disintegrants of the aforementioned (c) and (f) are the same or different and one or more kinds selected from carmellose calcium, low-substituted hydroxypropylcellulose and croscarmellose sodium.

[7] The film-coated tablet of the above-mentioned [6], wherein the cellulose-based disintegrants of the aforementioned (c) and (f) are the same or different and one or more kinds selected from carmellose calcium and low-substituted hydroxypropylcellulose.

[8] The film-coated tablet of the above-mentioned [6], wherein the cellulose-based disintegrant of the aforementioned (f) comprises carmellose calcium and low-substituted hydroxypropylcellulose.

[9] The film-coated tablet of any one of the above-mentioned [1] to [8], further comprising starch.

[10] The film-coated tablet of the above-mentioned [9], wherein the starch is natural starch.

[11] The film-coated tablet of the above-mentioned [9], wherein the starch is corn starch.

[12] The film-coated tablet of any one of the above-mentioned [1] to [11], wherein the water-soluble binder is one or more kinds selected from polyvinyl alcohol, hydroxypropylcellulose and hypromellose 2910.

[13] The film-coated tablet of the above-mentioned [12], wherein the water-soluble binder is one or more kinds selected from polyvinyl alcohol and hydroxypropylcellulose.

[14] The film-coated tablet of the above-mentioned [12], wherein the water-soluble binder is polyvinyl alcohol.

[15] The film-coated tablet of the above-mentioned [1] or [2], wherein the filler of the aforementioned (b) is lactose, the cellulose-based disintegrant of the aforementioned (c) is one or more kinds selected from carmellose calcium and low-substituted hydroxypropylcellulose, the water-soluble binder of the aforementioned (d) is one or more kinds selected from polyvinyl alcohol and hydroxypropylcellulose, the filler of the aforementioned (e) is lactose, and the cellulose-based disintegrant of the aforementioned (f) is one or more kinds selected from carmellose calcium and low-substituted hydroxypropylcellulose.

[16] The film-coated tablet of the above-mentioned [15], further comprising starch.

[17] The film-coated tablet of any one of the above-mentioned [1] to [16], having good dissolution property.

[18] A method of producing a film-coated tablet, comprising the following steps:
(1) a step of producing granulated particles by granulating a mixture containing compound A or a pharmaceutically acceptable salt thereof, (b) one or more kinds of fillers selected from lactose, D-mannitol, erythritol and crystalline cellulose, (c) a cellulose-based disintegrant and (d) a water-soluble binder;
(2) a step of producing a tablet by mixing the granulated particles obtained in step (1) with (e) one or more kinds of fillers selected from lactose, D-mannitol and crystalline cellulose and/or (f) a cellulose-based disintegrant, and forming the mixture; and
(3) a step of applying a film coating to the tablet obtained in step (2).

[19] The production method of the above-mentioned [18], wherein the filler of the aforementioned (b) is one or more kinds of fillers selected from lactose, D-mannitol and crystalline cellulose.

[20] The production method of the above-mentioned [18] or [19], wherein the filler of the aforementioned (b) is lactose, the cellulose-based disintegrant of the aforementioned (c) is one or more kinds selected from carmellose calcium and low-substituted hydroxypropylcellulose, the water-soluble binder of the aforementioned (d) is one or more kinds selected from polyvinyl alcohol and hydroxypropylcellulose, the filler of the aforementioned (e) is lactose, and the cellulose-based disintegrant of the aforementioned (f) is one or more kinds selected from carmellose calcium and low-substituted hydroxypropylcellulose.

[21] A tablet free of film coating, comprising (a) compound A or a pharmaceutically acceptable salt thereof, (b') one or more kinds of fillers selected from lactose and crystalline cellulose, (c) a cellulose-based disintegrant, (d) a water-soluble binder, and starch (hereinafter to be also referred to as tablet (I) of the present invention).

[22] The tablet of the above-mentioned [21], wherein the filler of the aforementioned (b') is lactose.

[23] A tablet obtained by mixing granulated particles obtained by granulating a mixture containing (a) compound A or a pharmaceutically acceptable salt thereof, (b) one or more kinds of fillers selected from lactose, D-mannitol, erythritol and crystalline cellulose, (c) a cellulose-based disintegrant and (d) a water-soluble binder with (e) one or more kinds of fillers selected from lactose, D-mannitol and crystalline cellulose and/or (f) a cellulose-based disintegrant, and forming the mixture (hereinafter to be also referred to as tablet (II) of the present invention).

[24] The tablet of the above-mentioned [23], wherein the filler of the aforementioned (b) is one or more kinds of fillers selected from lactose, D-mannitol and crystalline cellulose.

[25] The tablet of the above-mentioned [23] or [24], which is obtained by mixing granulated particles obtained by granulating a mixture of compound A or a pharmaceutically acceptable salt thereof, the filler(s) of (b), (c) a cellulose-based disintegrant and (d) a water-soluble binder, with (e) one or more kinds of fillers selected from lactose, D-mannitol and crystalline cellulose and (f) a cellulose-based disintegrant, and forming the mixture.

[26] The tablet of any one of the above-mentioned [23] to [25], which is free of film coating.

[27] The tablet of any one of the above-mentioned [21] to [26], showing good dissolution property.

Effect of the Invention

The tablets (I) and (II), and the film-coated tablet of the present invention (hereinafter these are to be also collectively referred to as the tablet of the present invention) have good dissolution property, and are useful as medicaments.

Tablet (II) of the present invention in itself shows good dissolution property, and further, is useful since the dissolution property does not decrease even when film coating is applied to give a film-coated tablet. The film-coated tablet of the present invention, which is obtained by applying a film coating to tablet (II) of the present invention, has superior properties in that it shows good storage stability by preventing decomposition by light with the shading film coating and shows good dissolution property.

Tablet (I) of the present invention is useful since it shows good dissolution property even without adding a later powder.

As used herein, in the present specification, the "tablet having good dissolution property" refers to a tablet showing a 15 min value of not less than 75% when the dissolution property is evaluated according to the Japanese Pharmacopoeia, 15th Edition, Dissolution Test Method (Paddle Method) and using diluted McIlvaine buffer adjusted to pH 5.0 as a test solution at rotation number 50 rpm. Furthermore, a preparation capable of maintaining the dissolution property (15 min value of not less than 75%) even after storage for a predetermined period (storage conditions and period here include storage for 2 weeks at 50° C. 85% RH, storage for one month at 40° C. 75% RH and the like) is preferable. More preferably, the 15 min value is not less than 85%, more preferably the 10 min value is not less than 70%. In addition, a tablet showing a 10 min value of not less than 70% when the dissolution property is evaluated according to the Paddle Method and using Japanese Pharmacopoeia, 15th Edition, 1st fluid for dissolution test (pH 1.2) as a test solution at rotation number 50 rpm is desirable.

BEST MODE FOR CARRYING OUT THE INVENTION

The present invention is explained in detail in the following.

The tablet (tablets (I), (II) and film-coated tablet) of the present invention contains compound A or a pharmaceutically acceptable salt thereof as an active component. The pharmaceutically acceptable salt is not particularly limited and, for example, salts with inorganic acid or organic acid can be mentioned. Examples of the inorganic acid include hydrochloric acid, hydrobromic acid, nitric acid, sulfuric acid, phosphoric acid and the like, and examples of the organic acid include formic acid, acetic acid, propionic acid, lactic acid, tartaric acid, oxalic acid, fumaric acid, maleic acid, citric acid, malonic acid, methanesulfonic acid, benzenesulfonic acid and the like. Preferred as a pharmaceutically acceptable salt of compound A is 3/2 fumarate of compound A. Compound A and a pharmaceutically acceptable salt thereof can be produced, for example, according to the method described in WO 03/016299 or a method analogous thereto.

The undersize D50% particle size of compound A or a pharmaceutically acceptable salt thereof is, for example, within the range of 0.1-10 μm, more preferably 0.5-5 μm, more preferably 0.5-3 μm. The undersize D90% particle size of compound A or a pharmaceutically acceptable salt thereof is, for example, within the range of 0.5-200 μm, more preferably 1-40 μm, more preferably 1-20 μm.

The above-mentioned particle sizes (undersize D50% particle size, undersize D90% particle size etc.) are values measured using a laser diffraction particle size distribution meter (dry method). For example, when a laser diffraction particle size distribution measurement apparatus HELOS & RODOS manufactured by Sympatec GmbH is used, measurement can be performed by setting the measurement range to R3 and the indication basis of the particle amount to volume basis.

The above-mentioned particle size is applied to compound A or a pharmaceutically acceptable salt thereof to be used as a starting material when producing the tablet of the present invention. In other words, the particle size of compound A or a pharmaceutically acceptable salt thereof may vary depending on the production process of the tablet of the present invention, coagulation during storage after production and the like. Examples of the production process causing such change include solid dispersion, inclusion and the like. Compound A or a pharmaceutically acceptable salt thereof having the above-mentioned particle size can be obtained by pulverizing according to a conventional method. The pulverization can be performed using, for example, a fluid energy mill such as spiral jet mill, jet-o-mill, counter jet mill, jet mill and the like, a hammer mill, a screen mill, a ball mill and the like, particularly preferably a fluid energy mill.

In the tablet of the present invention (tablets (I), (II) and film-coated tablet), the content of compound A or a pharmaceutically acceptable salt thereof in the granulated particles is generally 1-50 w/w %, preferably 5-35 w/w %, more preferably 10-30 w/w %.

In the tablet of the present invention (tablets (I), (II) and film-coated tablet), the content of compound A or a pharmaceutically acceptable salt thereof in the tablet is generally 1-40 w/w %, preferably 5-30 w/w %, more preferably 5-25 w/w %.

The film-coated tablet of the present invention is characteristically obtained by mixing granulated particles obtained by granulating a mixture of (a) compound A or a pharmaceutically acceptable salt thereof, (b) one or more kinds of fillers selected from lactose, D-mannitol, erythritol and crystalline cellulose, (c) a cellulose-based disintegrant and (d) a water-soluble binder, with (e) one or more kinds of fillers selected from lactose, D-mannitol and crystalline cellulose and/or (f) a cellulose-based disintegrant, forming the mixture to give a tablet and applying film coating to the tablet. In the present specification, component (e) and/or component (f) to be added to the granulated particles by mixing is/are to be also referred to as a later powder.

Tablet (II) of the present invention is characteristically obtained by mixing granulated particles obtained by granulating a mixture containing (a) compound A or a pharmaceutically acceptable salt thereof, (b) one or more kinds of fillers selected from lactose, D-mannitol, erythritol and crystalline cellulose, (c) a cellulose-based disintegrant and (d) a water-soluble binder with (e) one or more kinds of fillers selected from lactose, D-mannitol and crystalline cellulose and/or (f) a cellulose-based disintegrant, and forming the mixture.

Tablet (I) of the present invention is a tablet characterized by comprising (a) compound A or a pharmaceutically acceptable salt thereof, (b') one or more kinds of fillers selected from lactose and crystalline cellulose, (c) a cellulose-based disintegrant, (d) a water-soluble binder, and starch, and the absence of film coating. As tablet (I) of the present invention, a tablet wherein the filler of the aforementioned (b') is lactose is preferable.

In the film-coated tablet and tablet (II) of the present invention, the lactose, D-mannitol, erythritol and crystalline cellulose, which are the fillers of component (b), and lactose, D-mannitol and crystalline cellulose, which are the fillers of (e), are not limited as long as they are products usable for commercially available medicaments. The filler of (b) and the filler of (e) may be the same or different.

As the lactose and D-mannitol of component (e) to be used for a later powder, granulated lactose granulated in advance and granulated D-mannitol granulated in advance are preferable. Examples of the granulation method include agitation granulation method, fluid bed granulation method and spray dry granulation method. In addition, the granulated lactose and granulated D-mannitol to be used may be commercially available products. Examples of commercially available granulated lactose include FLowLac 100, Tablettose 70 (both trade names, manufactured by MEGGLE) and the like, and examples of the granulated D-mannitol include Parteck M 100 (trade name, manufactured by Merck & Co., Inc.), Pearlitol 300 DC (trade name, manufactured by Roquette) and the like.

As component (b), lactose and D-mannitol are preferable, and lactose is more preferable. As component (e), lactose (particularly, granulated lactose) and D-mannitol (particularly, granulated D-mannitol) are preferable, and lactose (particularly, granulated lactose) is more preferable.

In the film-coated tablet and tablet (II) of the present invention, the content of the total fillers of components (b) and (e) in the tablet is generally 30-95 w/w %, preferably 35-80 w/w %, more preferably 40-75 w/w %. The content of the filler of component (b) in the tablet is generally 10-90 w/w %, preferably 20-70 w/w %, more preferably 30-60 w/w %. The content of the filler of component (e) in the tablet is generally 0-70 w/w %, preferably 3-50 w/w %, more preferably 5-35 w/w %.

In tablet (I) of the present invention, lactose and crystalline cellulose, which are the fillers of component (b'), are not limited as long as they are products usable for commercially available medicaments. As component (b'), lactose is preferable.

In tablet (I) of the present invention, the content of the filler of component (b') in the tablet is generally 30-95 w/w %, preferably 35-80 w/w %, more preferably 40-75 w/w %.

In the tablet of the present invention (tablets (I), (II) and film-coated tablet), examples of the cellulose-based disintegrant of components (c) and (f) include carmellose calcium, low-substituted hydroxypropylcellulose, croscarmellose sodium, carmellose, carmellose sodium, crystalline cellulose and the like. In the film-coated tablet and tablet (II) of the present invention, the cellulose-based disintegrant of (c) and the cellulose-based disintegrant of (f) may be the same or different.

In the tablet of the present invention (tablets (I), (II) and film-coated tablet), as component (c), carmellose calcium, low-substituted hydroxypropylcellulose and croscarmellose sodium are preferable, and carmellose calcium and low-substituted hydroxypropylcellulose are more preferable. In the film-coated tablet and tablet (II) of the present invention, as component (f), carmellose calcium, low-substituted hydroxypropylcellulose and croscarmellose sodium are preferable, and carmellose calcium and low-substituted hydroxypropylcellulose are more preferable. As component (f), use of both carmellose calcium and low-substituted hydroxypropylcellulose is more preferable.

In the tablet of the present invention (tablets (I), (II) and film-coated tablet), as the low-substituted hydroxypropylcellulose of components (c) and (f), one having the content of a hydroxypropoxyl group of 10.0-12.9% and an average particle size of 17-65 μm is preferable, wherein the average particle size is more preferably 35-65 μm, further preferably 45-65 μm. Specific examples of the low-substituted hydroxypropylcellulose of components (c) and (f) include L-HPC (LH-11), L-HPC (LH-21) (both trade names, manufactured by Shin-Etsu Chemical Co., Ltd.) and the like.

In the film-coated tablet and tablet (II) of the present invention, the total content of the cellulose-based disintegrant of components (c) and (f) in the tablet is generally 3-40 w/w %, preferably 5-30 w/w %, more preferably 7-25 w/w %. The content of the cellulose-based disintegrant of component (c) in the tablet is generally 0.5-35 w/w %, preferably 1-20 w/w %, more preferably 2-10 w/w %. The content of the cellulose-based disintegrant of component (f) in the tablet is generally 0-35 w/w %, preferably 1-25 w/w %, more preferably 3-20 w/w %.

In tablet (I) of the present invention, the content of the cellulose-based disintegrant of component (c) in the tablet is generally 3-40 w/w %, preferably 5-30 w/w %, more preferably 7-25 w/w %.

In the tablet of the present invention (tablets (I), (II) and film-coated tablet), the water-soluble binder of component (d) is not particularly limited as long as it can dissolve in water. Examples thereof include, polyvinyl alcohol, hydroxypropylcellulose, hypromellose 2910, gum arabic, pregelatinized starch, agar, polyvinylpyrrolidone, gelatin, hypromellose 2906 and the like. Preferred are polyvinyl alcohol, hydroxypropylcellulose and hypromellose 2910, more preferred are polyvinyl alcohol and hydroxypropylcellulose, and further preferred is polyvinyl alcohol.

In the tablet of the present invention (tablets (I), (II) and film-coated tablet), preferable examples of polyvinyl alcohol, which is the water-soluble binder of component (d), include those having a saponification degree of not less than 85.0% and viscosity of 2.0-10.0 mPa·s, wherein more preferred are those having a saponification degree of not less than 86.5% and viscosity of 2.0-7.0 mPa·s, and further preferred are those having a saponification degree of 86.5-89.0% and viscosity of 4.8-5.8 mPa·s. Specific examples of polyvinyl alcohol, which is the water-soluble binder of component (d), include GOHSENOL EG-05 (trade name, manufactured by Nippon Synthetic Chemical Industry Co., Ltd.) and the like.

In the tablet of the present invention (tablets (I), (II) and film-coated tablet), preferable examples of the hydroxypropylcellulose which is the water-soluble binder of component (d) include those having a viscosity of 3.0-10.0 mPa·s, more preferably 6.0-10.0 mPa·s. Specific examples of hydroxypropylcellulose, which is the water-soluble binder of component (d), include HPC-L, HPC-SL (both trade names, manufactured by NIPPON SODA CO., LTD.) and the like.

In the tablet of the present invention (tablets (I), (II) and film-coated tablet), preferable examples of hypromellose 2910, which is the water-soluble binder of component (d), include those having a viscosity of 2.5-7.0 mPa·s, more preferably 2.5-5.1 mPa·s, further preferably 2.5-3.5 mPa·s. Specific examples of hypromellose 2910, which is the water-soluble binder of component (d), include TC-5E, TC-5M, TC-5R (both trade names, manufactured by Shin-Etsu Chemical Co., Ltd.) and the like.

In the tablet of the present invention (tablets (I), (II) and film-coated tablet), the content of the water-soluble binder of component (d) in the tablet is generally 0.1-10 w/w %, preferably 0.5-5 w/w %, more preferably 1-3 w/w %.

Examples of the coating agent to be used for the film-coated tablet of the present invention include a combination of a substrate such as hypromellose, hydroxypropylcellulose, polyvinylpyrrolidone and the like, and a plasticizer such as polyethylene glycol, propylene glycol, triacetine, triethyl citrate, glycerol, glycerin fatty acid ester etc., and the like. In addition, additives such as titanium oxide, mannitol and the like may be added as necessary.

As the substrate of the coating agent to be used for the film-coated tablet of the present invention, a water-soluble substrate such as hypromellose 2910, hydroxypropylcellulose, polyvinylpyrrolidone, polyvinyl alcohol and the like are preferable, and hypromellose 2910 is more preferable. Examples of hypromellose 2910, which is a coating agent, include those having a viscosity of 2.5-7.0 mPa·s. As the plasticizer, polyethylene glycol, propylene glycol, triacetine, triethyl citrate, glycerol and the like are preferable, and polyethylene glycol is more preferable.

The coating agent may further contain additives usable for pharmaceutical products as long as it does not influence the effect of the film. Examples of the additives include light shielding agent, colorant, flavor and the like. Particularly, addition of a light shielding agent is desirable. As the light shielding agent, metal oxides such as titanium oxide, red ferric oxide, zinc oxide and the like, calcium salts such as calcium fluoride, calcium chloride, calcium bromide, calcium carbonate, calcium hydrogencarbonate, calcium phosphate, calcium hydrogen phosphate, calcium monohydrogen phosphate, calcium dihydrogen pyrophosphate, calcium silicate, calcium sulfate, calcium hydrogensulfate, calcium nitrate, calcium stearate, calcium lactate and the like, magnesium salt such as magnesium hydrogenphosphate, magnesium carbonate, magnesium fluoride, magnesium silicate, magnesium stearate and the like, talc, kaolin and the like are preferable, and titanium oxide is more preferable. Examples of the colorant include yellow ferric oxide, red ferric oxide, riboflavine (riboflavin, riboflavin sodium phosphate), water-soluble food tar color (Food Color Red Nos. 2 and 3, Food Color yellow Nos. 4 and 5, Food Color blue No. 1 etc.), water insoluble lake dye (aluminum salt of the above-mentioned water-soluble food tar color, etc.), natural dye (e.g., β-carotene, chlorophyll etc.) and the like. These may also be added as the light shielding agent.

As a coating agent to be used for the film-coated tablet of the present invention, a shading coating agent is preferable. Examples of the shading coating agent include the above-mentioned light shielding agents (particularly, titanium oxide) and/or a coating agent containing the above-mentioned colorant and the like. Preferred is a coating agent containing titanium oxide.

Preferable examples of the coating agent include Opadry (registered trade mark; a mixture of hypromellose 2910 about 71%, polyethylene glycol 400 about 7%, and titanium oxide about 22%).

The amount of the coating agent to be used is generally 0.1-10 w/w %, preferably 0.5-5 w/w %, more preferably 1-4 w/w %, relative to the tablet.

Where necessary, the film-coated tablet and tablet (II) of the present invention may contain, besides the above mentioned components, excipients used in the field of preparations (e.g., fillers other than those of components (b) and (e) (i.e., lactose, D-mannitol, erythritol and crystalline cellulose), disintegrants other than cellulose-based disintegrants of component (c) (e.g., starch, light anhydrous silicic acid), lubricant, fluidizer, flavor, colorant, corrigent etc.). Where necessary, tablet (I) of the present invention may contain, besides the above-mentioned components, additives used in the field of preparations (e.g., fillers other than those of component (b') (i.e., lactose and crystalline cellulose), disintegrants other than starch and the cellulose-based disintegrants of component (c) (e.g., light anhydrous silicic acid), lubricant, fluidizer, flavor, colorant, corrigent etc.).

These additives may be added in any step during the production of the tablet of the present invention, and may be added between step and step.

The film-coated tablet and tablet (II) of the present invention preferably contain starch. Examples of the starch include unprocessed natural starch such as corn starch, potato starch, rice starch and wheat starch, partly pregelatinized starch wherein a part is gelatinized, and chemically modified starch such as sodium carboxymethyl starch. Preferred is natural starch, and more preferred is corn starch. While starch is not particularly limited, for example, it may be added during the production step of granulated particles, or may be added during the step of mixing granulated particles and a later powder and forming the mixture into tablets.

In the film-coated tablet and tablet (II) of the present invention, the content of the starch in the tablet is generally 0.1-50 w/w %, preferably 0.5-30 w/w %, more preferably 1-10 w/w %.

The tablet (I) of the present invention contains starch. Examples of the starch in tablet (I) include unprocessed natural starch such as corn starch, potato starch, rice starch and wheat starch, partly pregelatinized starch wherein a part is gelatinized, and chemically modified starch such as sodium carboxymethyl starch. Preferred is natural starch, and more preferred is corn starch.

In tablet (I), the content of starch in the tablet is preferably 0.1-50 w/w %, more preferably 0.5-30 w/w %, still more preferably 1-10 w/w %.

The tablet (tablet (I), (II) and film-coated tablet) of the present invention preferably contains a lubricant. As the lubricant, magnesium stearate, calcium stearate and sodium stearyl fumarate can be mentioned. The content of the lubricant in the tablet is generally about 0.3-about 3 w/w %, preferably about 0.5-about 1.5 w/w %.

The film-coated tablet of the present invention can be produced by using the above-mentioned components and by the following steps (1)-(3):

(1) a step of producing granulated particles by granulating a mixture containing (a) compound A or a pharmaceutically acceptable salt thereof, (b) one or more kinds of fillers selected from lactose, D-mannitol, erythritol and crystalline cellulose, (c) a cellulose-based disintegrant and (d) a water-soluble binder;

(2) a step of producing a tablet by mixing the granulated particles obtained in step (1) with (e) one or more kinds of fillers selected from lactose, D-mannitol and crystalline cellulose and/or (f) a cellulose-based disintegrant, and forming the mixture; and (3) a step of applying a film coating to the tablet obtained in step (2).

In more detail, the film-coated tablet of the present invention can be produced by using the above-mentioned components and, for example, by the following method.

Production Method 1

(1) Preparation of Binding Solution

A binding solution can be prepared by dissolving a water-soluble binder in purified water. The temperature during dissolution is, for example, about 20° C.-about 90° C., preferably about 20° C.-about 70° C. The concentration of the binder in a binding solution is, for example, about 1-about 20 wt %, preferably about 2-about 5 wt %.

(2) Preparation of Granulated Particles

Compound A or a pharmaceutically acceptable salt thereof, a filler, a cellulose-based disintegrant and starch, when starch is to be contained, are charged in a fluid bed granulator and mixed. Then, the mixture is granulated while spraying the binding solution of (1). The charge air temperature during granulation is about 50° C.-about 90° C., preferably about 60° C.-about 80° C. The granulation time is about 30-about 180 min, preferably about 40-about 150 min. As the granulating machine, a fluid bed granulator, a tumbling fluid bed granulator and the like can be used.

(3) Drying of Granulated Particles

The granulated particles of (2) are dried under reduced pressure or normal pressure. The drying is preferably performed such that the value of loss on drying observed by an infrared ray moisture meter is, for example, within about 3 wt %, preferably within about 2 wt %. Where necessary, the particle size is adjusted using a sieving machine after drying. As the sieving machine, for example, a sieve shaker and a screen mill can be mentioned.

(4) Mixing of Later Powder and Lubricant

The granulated particles of (3) are mixed with a later powder and a lubricant. The later powder only needs to contain one or more kinds selected from lactose, D-mannitol, crystalline cellulose and cellulose-based disintegrant and, where necessary, a filler other than lactose, D-mannitol and crystalline cellulose, a disintegrant other than those based on cellulose, a fluidizer, a flavor, a colorant, a corrigent and the like may be added. A later powder and a lubricant can be mixed by adding a later powder and a lubricant in a mixer containing granulated particles of (3). A later powder and a lubricant may be simultaneously added, or sequentially added. As a mixer, an agitation mixer [tumble] and the like can be mentioned. Specifically, a tumbler blender, a V-blender, a double cone, a bin tumbler and the like can be used.

(5) Tabletting

The mixed granules obtained in (4) are tabletted by a conventional method to give a tablet. As a tabletting machine, a single punch tabletting machine, a rotary tabletting machine and the like can be used. The tablet hardness is, for example, about 30-about 200 N.

(6) Film Coating and Drying

The tablet of (5) is subjected to film coating by a conventional method. Examples of the coating apparatus include coating pan and the like, specifically, an aeration type coating system (Perforated Coating System) and the like. After the film coating treatment, the tablet is dried at about 40-90° C., whereby the film-coated tablet of the present invention can be produced.

Production Method 2

(1) Preparation of Binding Solution

In the same manner as in (1) of production method 1, a binding solution is prepared. The concentration of the binder in the binding solution is, for example, about 1-about 40 wt %, preferably about 5-about 30 wt %.

(2) Preparation of Granulated Particles

Compound A or a pharmaceutically acceptable salt thereof, filler, cellulose-based disintegrant and starch, when starch is to be contained, are charged in an agitation granulator and mixed. Then, the mixture is granulated while spraying the binding solution of (1). As the granulating machine, a vertical granulator, a ponymixer, a kneader and the like can be used.

(3) Drying of Granulated Particles, Mixing of Later Powder and Lubricant, Tabletting, Film Coating and Drying of Tablet In the same manner as in (3) to (6) of production method 1, the film-coated tablet of the present invention can be produced.

The tablet (I) of the present invention can be produced in the same manner as in the film-coated tablet of the present invention except that the addition of a later powder is optional, the film coating step is not included, the aforementioned component (b') is used instead of the aforementioned component (b) and starch is added. Starch may be added in any step during the production, and may be added, for example, in the production step of granulated particles or in the step of forming granulated particles into tablets. Addition in the production step of granulated particles is preferable. The tablet (I) of the present invention can also be produced by mixing and tabletting the aforementioned components (a), (b'), (c) and (d), starch and any excipient by a method known per se.

The tablet (II) of the present invention can be produced in the same manner as in the film-coated tablet of the present invention except that the film coating step is not necessary.

The tablet (tablets (I), (II) and film-coated tablet) of the present invention can be orally administered to mammals (e.g., mouse, rat, rabbit, cat, dog, bovine, horse, monkey, human).

While the dose of the tablet (tablets (I), (II) and film-coated tablet) of the present invention varies depending on the subject of administration (age, body weight etc.), severity of disease and the like, it can be selected from the range where the dose of compound A or a pharmaceutically acceptable salt thereof is an effective amount. Specifically, for example, the amount of compound A is generally 0.1-2000 mg/day, preferably 1-200 mg/day, for one adult, which may be administered once or several portions (for example, 2-4 portions) per day.

EXAMPLES

The present invention is explained in more detail in the following by referring to Examples, which are not to be construed as limitative.

The particle size of 3/2 fumarate of compound A used in the following Examples was 0.5-3 μm for undersize D50% and 1-12 μm for undersize D90% particle size, as measured by a dry method using a laser diffraction particle size distribution measurement apparatus, HELOS&RODOS, manufactured by Sympatec GmbH.

In the present specification, the abbreviation means the following.

CMC-Ca: carmellose calcium
L-HPC: low-substituted hydroxypropylcellulose
croscarmellose Na: croscarmellose sodium
PVA: polyvinyl alcohol
HPC-L: hydroxypropylcellulose
HPMC: hypromellose 2910
Mg-St: magnesium stearate
Ca-St: calcium stearate
PRUV: sodium stearyl fumarate In the Examples and Comparative Examples, the following was used.

lactose: Pharmatose 200M (trade name, manufactured by DMV-Fonterra Excipients)
granulated lactose: FLowLac 100 (trade name, manufactured by MEGGLE) (Tables 2, 3, 4); Tablettose 70 (trade name, manufactured by MEGGLE) (Tables 6, 8, 9, 10)
granulated D-mannitol: Parteck M 100 (trade name, manufactured by Merck & Co., Inc.)
crystalline cellulose: CEOLUS PH101 (trade name, manufactured by Asahi Kasei Chemicals Corporation)
L-HPC: L-HPC (LH-11) (trade name, manufactured by Shin-Etsu Chemical Co., Ltd.) (Tables 2, 3, 4); L-HPC (LH-21) (trade name, manufactured by Shin-Etsu Chemical Co., Ltd.) (Tables 8, 9)
crospovidone: Kollidon-CL (trade name, manufactured by BSAF) PVA: GOHSENOL EG-05 (trade name, manufactured by Nippon Synthetic Chemical Industry Co., Ltd.)
HPC-L: HPC-L (trade name, manufactured by NIPPON SODA CO., LTD.)
HPMC: TC-5E (trade name, manufactured by Shin-Etsu Chemical Co., Ltd.)

Production Example 1

Components for granulated particles other than the binder (PVA) in the formulations shown in Table 1 were charged in a fluid bed granulator, granulated while spraying a binding solution, and dried to give granulated particles. The obtained granulated particles were charged in a blender and mixed with a lubricant. The mixture was tabletted by a tabletting machine to give tablets of Examples 1 and 2 and Comparative Examples 1-4.

TABLE 1

| | | formulation No. | | | | | |
| --- | --- | --- | --- | --- | --- | --- | --- |
| | | Ex. 1 | Comp. Ex. 1 | Comp. Ex. 2 | Comp. Ex. 3 | Ex. 2 | Comp. Ex. 4 |
| granulated particles | compound A 3/2 fumarate | 40 | 40 | 40 | 40 | 40 | 40 |
| | lactose | 120 | — | — | — | — | — |
| | sucrose | — | 120 | — | — | — | — |
| | D-mannitol | — | — | 120 | — | — | — |
| | erythritol | — | — | — | 120 | — | — |

TABLE 1-continued

| | | Ex. 1 | Comp. Ex. 1 | Comp. Ex. 2 | Comp. Ex. 3 | Ex. 2 | Comp. Ex. 4 |
|---|---|---|---|---|---|---|---|
| | crystalline cellulose | — | — | — | — | 120 | — |
| | anhydrous dibasic calcium phosphate | — | — | — | — | — | 120 |
| | corn starch | 9 | 9 | 9 | 9 | 9 | 9 |
| | CMC-Ca | 12 | 12 | 12 | 12 | 12 | 12 |
| | PVA | 4.8 | 4.8 | 4.8 | 4.8 | 4.8 | 4.8 |
| | (purified water) | (128.5) | (128.5) | (128.5) | (128.5) | (128.5) | (128.5) |
| granulated particles subtotal | | 185.8 | 185.8 | 185.8 | 185.8 | 185.8 | 185.8 |
| lubricant | Mg-St | 1.9 | 1.9 | 1.9 | 1.9 | 1.9 | 1.9 |
| total | | 187.7 | 187.7 | 187.7 | 187.7 | 187.7 | 187.7 |
| dissolution rate (%) | | | | | | | |
| INITIAL 10 min | | 74 | 4 | 16 | 20 | 67 | 18 |
| INITIAL 15 min | | 89 | 7 | 29 | 33 | 77 | 20 |
| 50° C. 85% × 2W 15 min | | 79 | — | — | — | 61 | — |

In the Table, "INITIAL 10 min" shows the dissolution rate of non-stored product at 10 min after the start of the dissolution test, "INITIAL 15 min" shows the dissolution rate of non-stored product at 15 min after the start of the dissolution test, and "50° C. 85% × 2W 15 min" shows the dissolution rate of stored product at 15 min after the start of the dissolution test. The numerical values of each component and the total show weight (mg) per tablet.

Production Example 2

Components for granulated particles other than the binder (PVA) in the formulations shown in Tables 2-4 were charged in a fluid bed granulator, granulated while spraying a binding solution, and dried to give granulated particles. The obtained granulated particles were charged in a blender and mixed with a later powder component and a lubricant. The mixture was tabletted by a tabletting machine to give tablets (core tablets). The obtained tablets were charged in a coating machine, and a coating solution was sprayed to achieve a predetermined film amount and dried to give film-coated tablets of Examples 3-15 and Comparative Examples 5-8.

TABLE 2

| | | Ex. 3 | Comp. Ex. 5 | Ex. 4 | Ex. 5 | Ex. 6 | Comp. Ex. 6 |
|---|---|---|---|---|---|---|---|
| granulated particles | compound A 3/2 fumarate | 40 | 40 | 40 | 40 | 40 | 40 |
| | lactose | 120 | — | — | — | — | — |
| | sucrose | — | 120 | — | — | — | — |
| | D-mannitol | — | — | 120 | — | — | — |
| | erythritol | — | — | — | 120 | — | — |
| | crystalline cellulose | — | — | — | — | 120 | — |
| | anhydrous dibasic calcium phosphate | — | — | — | — | — | 120 |
| | corn starch | 9 | 9 | 9 | 9 | 9 | 9 |
| | CMC-Ca | 12 | 12 | 12 | 12 | 12 | 12 |
| | PVA | 4.8 | 4.8 | 4.8 | 4.8 | 4.8 | 4.8 |
| | (purified water) | (128.5) | (128.5) | (128.5) | (128.5) | (128.5) | (128.5) |
| granulated particles subtotal | | 185.8 | 185.8 | 185.8 | 185.8 | 185.8 | 185.8 |
| later powder | granulated lactose | 20.8 | 20.8 | 20.8 | 20.8 | 20.8 | 20.8 |
| | CMC-Ca | 12 | 12 | 12 | 12 | 12 | 12 |
| | L-HPC | 19 | 19 | 19 | 19 | 19 | 19 |
| lubricant | Mg-St | 2.4 | 2.4 | 2.4 | 2.4 | 2.4 | 2.4 |
| coating agent | Opadry (trade mark) | 5 | 5 | 5 | 5 | 5 | 5 |
| total | | 245 | 245 | 245 | 245 | 245 | 245 |
| dissolution rate (%) | | | | | | | |
| INITIAL 10 min | | 94 | 28 | 74 | 64 | 80 | 49 |

TABLE 2-continued

| | formulation No. | | | | | |
|---|---|---|---|---|---|---|
| | Ex. 3 | Comp. Ex. 5 | Ex. 4 | Ex. 5 | Ex. 6 | Comp. Ex. 6 |
| INITIAL 15 min | 100 | 45 | 99 | 91 | 89 | 52 |
| 50° C. 85% × 2W 15 min | 91 | — | 88 | 4 | 83 | — |

In the Table, "INITIAL 10 min" shows the dissolution rate of non-stored product at 10 min after the start of the dissolution test, "INITIAL 15 min" shows the dissolution rate of non-stored product at 15 min after the start of the dissolution test, and "50° C. 85% × 2W 15 min" shows the dissolution rate of stored product at 15 min after the start of the dissolution test. The numerical values of each component and the total show weight (mg) per tablet.

TABLE 3

| | | formulation No. | | | | | |
|---|---|---|---|---|---|---|---|
| | | Comp. Ex. 7 | Ex. 7 | Ex. 8 | Ex. 9 | Ex. 10 | Ex. 11 |
| granulated particles | compound A 3/2 fumarate | 40 | 40 | 40 | 40 | 40 | 40 |
| | lactose | 120 | 120 | 120 | 120 | 120 | 120 |
| | corn starch | 9 | 9 | 9 | 9 | 9 | 9 |
| | CMC-Ca | 12 | 12 | 12 | 12 | 12 | 12 |
| | PVA | 4.8 | 4.8 | 4.8 | 4.8 | 4.8 | 4.8 |
| | (purified water) | (128.5) | (128.5) | (128.5) | (128.5) | (128.5) | (128.5) |
| granulated particles subtotal | | 185.8 | 185.8 | 185.8 | 185.8 | 185.8 | 185.8 |
| later powder | granulated lactose | — | 51.8 | — | 20.8 | 20.8 | — |
| | granulated D-mannitol | — | — | — | — | — | 20.8 |
| | CMC-Ca | — | — | 12 | 31 | — | 12 |
| | L-HPC | — | — | 19 | — | 31 | 19 |
| lubricant | Mg-St | 1.9 | 2.4 | 2.2 | 2.4 | 2.4 | 2.4 |
| coating agent | Opadry (trade mark) | 4 | 5 | 5 | 5 | 5 | 5 |
| total | | 191.7 | 245 | 224 | 245 | 245 | 245 |
| dissolution rate (%) | | | | | | | |
| INITIAL 10 min | | 36 | 66 | 64 | 94 | 87 | 76 |
| INITIAL 15 min | | 66 | 84 | 89 | 101 | 98 | 94 |
| 50° C. 85% × 2W 15 min | | — | 76 | 90 | 90 | 92 | 91 |

In the Table, "INITIAL 10 min" shows the dissolution rate of non-stored product at 10 min after the start of the dissolution test, "INITIAL 15 min" shows the dissolution rate of non-stored product at 15 min after the start of the dissolution test, and "50° C. 85% × 2W 15 min" shows the dissolution rate of stored product at 15 min after the start of the dissolution test. The numerical values of each component and the total show weight (mg) per tablet.

TABLE 4

| | | formulation No. | | | | |
|---|---|---|---|---|---|---|
| | | Comp. Ex. 8 | Ex. 12 | Ex. 13 | Ex. 14 | Ex. 15 |
| granulated particles | compound A •3/2 fumarate | 40 | 40 | 40 | 40 | 40 |
| | D-mannitol | 120 | 120 | 120 | 120 | 120 |
| | corn starch | 9 | 9 | 9 | 9 | 9 |
| | CMC-Ca | 12 | 12 | 12 | 12 | 12 |
| | PVA | 4.8 | 4.8 | 4.8 | 4.8 | 4.8 |
| | (purified water) | (128.5) | (128.5) | (128.5) | (128.5) | (128.5) |
| granulated particles subtotal | | 185.8 | 185.8 | 185.8 | 185.8 | 185.8 |
| later powder | granulated lactose | — | — | 20.8 | 20.8 | — |
| | granulated D-mannitol | — | — | — | — | 20.8 |
| | CMC-Ca | — | 12 | 31 | — | 12 |
| | L-HPC | — | 19 | — | 31 | 19 |
| lubricant | Mg-St | 1.9 | 2.2 | 2.4 | 2.4 | 2.4 |
| coating agent | Opadry (trade mark) | 4 | 5 | 5 | 5 | 5 |
| total | | 191.7 | 224 | 245 | 245 | 245 |

TABLE 4-continued

|  | formulation No. | | | | |
| --- | --- | --- | --- | --- | --- |
|  | Comp. Ex. 8 | Ex. 12 | Ex. 13 | Ex. 14 | Ex. 15 |
| dissolution rate (%) | | | | | |
| INITIAL 10 min | 24 | 61 | 81 | 62 | 77 |
| INITIAL 15 min | 43 | 92 | 98 | 91 | 96 |
| 50° C. 85% × 2W 15 min | — | 87 | 88 | 83 | 87 |

In the Table, "INITIAL 10 min" shows the dissolution rate of non-stored product at 10 min after the start of the dissolution test, "INITIAL 15 min" shows the dissolution rate of non-stored product at 15 min after the start of the dissolution test, and "50° C. 85% × 2W 15 min" shows the dissolution rate of stored product at 15 min after the start of the dissolution test. The numerical values of each component and the total show weight (mg) per tablet.

Production Example 3

In the same manner as in Production Example 1 in the formulation shown in Table 5, the tablets of Examples 16 and 17, and Comparative Example 9 were obtained.

TABLE 5

|  |  | formulation No. | | |
| --- | --- | --- | --- | --- |
|  |  | Ex. 16 | Ex. 17 | Comp. Ex. 9 |
| granulated particles | compound A•3/2 fumarate | 60 | 60 | 60 |
|  | lactose | 127 | 130 | 130 |
|  | corn starch | 13.8 | 13.8 | 13.8 |
|  | CMC-Ca | 18 | — | — |
|  | croscarmellose Na | — | 11 | — |
|  | crospovidone | — | — | 11 |
|  | light anhydrous silicic acid | 4 | — | — |
|  | PVA | 4.8 | 4.8 | 4.8 |
|  | (purified water) | (235.2) | (235.2) | (235.2) |
| granulated particles subtotal |  | 227.6 | 219.6 | 219.6 |
| lubricant | Mg-St | 2.4 | 2.4 | 2.4 |
| total |  | 230 | 222 | 222 |
| dissolution rate (%) | | | | |
| INITIAL 10 min | | 66 | 68 | 26 |
| INITIAL 15 min | | 80 | 80 | 35 |

In the Table, "INITIAL 10 min" shows the dissolution rate at 10 min after the start of the dissolution test, and "INITIAL 15 min" shows the dissolution rate at 15 min after the start of the dissolution test. The numerical values of each component and the total show weight (mg) per tablet.

Production Example 4

In the same manner as in Production Example 2 in the formulation shown in Table 6, the film-coated tablets of Examples 18 and 19, and Comparative Example 10 were obtained.

TABLE 6

|  |  | formulation No. | | |
| --- | --- | --- | --- | --- |
|  |  | Ex. 18 | Ex. 19 | Comp. Ex. 10 |
| granulated particles | compound A•3/2 fumarate | 60 | 60 | 60 |
|  | lactose | 123 | 130 | 130 |
|  | corn starch | 13.8 | 13.8 | 13.8 |
|  | CMC-Ca | 18 | — | — |
|  | croscarmellose Na | — | 11 | — |
|  | crospovidone | — | — | 11 |
|  | PVA | 7.2 | 4.8 | 4.8 |
|  | (purified water) | (240) | (240) | (240) |
| granulated particles subtotal |  | 222 | 219.6 | 219.6 |
| later powder | granulated lactose | 19 | 26.4 | 26.4 |
|  | CMC-Ca | 13.3 | — | — |
|  | partly pregelatinized starch | — | 13.3 | 13.3 |
|  | croscarmellose Na | — | 8 | — |
|  | crospovidone | — | — | 8 |
| lubricant | Mg-St | 2.7 | 2.7 | 2.7 |
| coating agent | Opadry (trade mark) | 5 | 5 | 5 |
| total |  | 262 | 275 | 275 |
| dissolution rate (%) | | | | |
| core tablet 10 min | | 53 | 69 | 60 |
| core tablet 15 min | | 77 | 80 | 70 |
| film-coated tablet 15 min | | 76 | 82 | 71 |

In the Table, "core tablet 10 min" shows the dissolution rate of the core tablet at 10 min after the start of the dissolution test, "core tablet 15 min" shows the dissolution rate of the core tablet at 15 min after the start of the dissolution test, and "film-coated tablet 15 min" shows the dissolution rate of the film-coated tablet at 15 min after the start of the dissolution test. The numerical values of each component and the total show weight (mg) per tablet.

Production Example 5

In the same manner as in Production Example 1 in the formulation shown in Table 7, the tablets of Examples 20-22, and Comparative Example 11 were obtained.

TABLE 7

|  |  | formulation No. | | | |
| --- | --- | --- | --- | --- | --- |
|  |  | Comp. Ex. 11 | Ex. 20 | Ex. 21 | Ex. 22 |
| granulated particles | compound A•3/2 fumarate | 5 | 5 | 5 | 5 |
|  | lactose | 68.6 | 61.74 | 48.02 | 34.3 |
|  | corn starch | — | 6.86 | 20.58 | 34.3 |
|  | CMC-Ca | 4 | 4 | 4 | 4 |
|  | PVA | 1.6 | 1.6 | 1.6 | 1.6 |
|  | (purified water) | (30.4) | (30.4) | (30.4) | (30.4) |
| granulated particles subtotal |  | 79.2 | 79.2 | 79.2 | 79.2 |
| lubricant | Mg-St | 0.8 | 0.8 | 0.8 | 0.8 |
| total |  | 80 | 80 | 80 | 80 |

TABLE 7-continued

| | formulation No. | | | |
|---|---|---|---|---|
| | Comp. Ex. 11 | Ex. 20 | Ex. 21 | Ex. 22 |
| dissolution rate (%) 15 min core tablet | 57 | 103 | 85 | 92 |

In the Table the dissolution rate shows that at 15 min after the start of the dissolution test. The numerical values of each component and the total show weight (mg) per tablet.

Production Example 6

Components for granulated particles other than the binder (PVA, HPC-L or HPMC) in the formulations shown in Tables 8 and were charged in a fluid bed granulator, granulated while spraying a binding solution, and dried to give granulated particles. The obtained granulated particles were charged in a blender and mixed with a later powder component and a lubricant. The mixture was tabletted by a tabletting machine to give tablets (core tablets). The obtained tablets were charged in a coating machine, and a coating solution was sprayed to achieve a predetermined film amount and dried to give the film-coated tablets of Examples 23-28.

TABLE 8

| | | formulation No. | | |
|---|---|---|---|---|
| | | Ex. 23 | Ex. 24 | Ex. 25 |
| granulated particles | compound A•3/2 fumarate | 40 | 40 | 40 |
| | lactose | 82 | 82 | 82 |
| | corn starch | 9 | 9 | 9 |
| | CMC-Ca | 12 | 12 | 12 |
| | PVA | 3.2 | — | — |
| | HPC-L | — | 3.2 | — |
| | HPMC | — | — | 4.8 |
| | (purified water) | (156.8) | (156.8) | (155.2) |
| granulated particles subtotal | | 146.2 | 146.2 | 147.8 |
| later powder | granulated lactose | 9 | 9 | 7.4 |
| | CMC-Ca | 8.8 | 9 | 9 |
| | L-HPC | 14.2 | 14 | 14 |

TABLE 8-continued

| | | formulation No. | | |
|---|---|---|---|---|
| | | Ex. 23 | Ex. 24 | Ex. 25 |
| lubricant | Mg-St | 1.8 | 1.8 | 1.8 |
| coating agent | Opadry (trade mark) | 4 | 4 | 4 |
| total | | 184 | 184 | 184 |
| dissolution rate (%) 15 min film-coated tablet | | 88 | 87 | 77 |

In the Table the dissolution rate shows that at 15 min after the start of the dissolution test. The numerical values of each component and the total show weight (mg) per tablet.

TABLE 9

| | | formulation No. | | |
|---|---|---|---|---|
| | | Ex. 26 | Ex. 27 | Ex. 28 |
| granulated particles | compound A•3/2 fumarate | 40 | 40 | 40 |
| | lactose | 82 | 82 | 82 |
| | corn starch | 9 | 9 | 9 |
| | CMC-Ca | 12 | 12 | 12 |
| | PVA | 3.2 | 3.2 | 3.2 |
| | (purified water) | (103.5) | (103.5) | (103.5) |
| granulated particles subtotal | | 146.2 | 146.2 | 146.2 |
| later powder | granulated lactose | 9 | 8.1 | 5.4 |
| | CMC-Ca | 9 | 9 | 9 |
| | L-HPC | 14 | 14 | 14 |
| lubricant | Mg-St | 1.8 | — | — |
| | Ca-St | — | 2.7 | — |
| | PRUV | — | — | 5.4 |
| coating agent | Opadry (trade mark) | 4 | 4 | 4 |
| total | | 184 | 184 | 184 |
| dissolution rate (%) 15 min film-coated tablet | | 82 | 84 | 88 |

In the Table the dissolution rate shows that at 15 min after the start of the dissolution test. The numerical values of each component and the total show weight (mg) per tablet.

Production Example 7

In the same manner as in Production Example 2 in the formulation shown in Table 10, the film-coated tablets of Examples 29-34 were obtained.

TABLE 10

| | | formulation No. | | | | | |
|---|---|---|---|---|---|---|---|
| | | Ex. 29 | Ex. 30 | Ex. 31 | Ex. 32 | Ex. 33 | Ex. 34 |
| granulated particles | compound A 3/2 fumarate | 60 | 60 | 60 | 60 | 60 | 60 |
| | lactose | 300 | 182 | 123 | 123 | 123 | 123 |
| | corn starch | 33.6 | 20.4 | 13.8 | 13.8 | 13.8 | 13.8 |
| | CMC-Ca | 36 | 24 | 18 | 18 | 18 | 18 |
| | PVA | 9.6 | 6.4 | 7.2 | 7.2 | 7.2 | 7.2 |
| | (purified water) | (310.4) | (206.9) | (232.8) | (232.8) | (232.8) | (232.8) |
| granulated particles subtotal | | 439.2 | 292.8 | 222 | 222 | 222 | 222 |
| later powder | granulated lactose | 216 | 144 | 105.6 | 51 | 19 | — |
| | CMC-Ca | 36 | 24 | 18 | 15 | 13.3 | 11.8 |
| | L-HPC | — | — | — | — | — | — |
| | light anhydrous silicic acid | 21.6 | 14.4 | 10.8 | 9 | 8 | 7.2 |

TABLE 10-continued

| | | formulation No. | | | | | |
| --- | --- | --- | --- | --- | --- | --- | --- |
| | | Ex. 29 | Ex. 30 | Ex. 31 | Ex. 32 | Ex. 33 | Ex. 34 |
| lubricant | Mg-St | 7.2 | 4.8 | 3.6 | 3 | 2.7 | 2.4 |
| coating agent | Opadry (trade mark) | 10 | 8 | 6 | 6 | 5 | 5 |
| total | | 730 | 488 | 366 | 306 | 270 | 248.4 |
| dissolution rate (%) 15 min | | | | | | | |
| core tablet | | 92 | 91 | 91 | 91 | 92 | 92 |
| film-coated tablet | | 88 | 90 | 87 | 88 | 90 | 87 |

In the Table, the dissolution rate shows that at 15 min after the start of the dissolution test. The numberical values of each component and the total show weight (mg) per tablet.

Experimental Example 1

The tablets or film-coated tablets obtained in Production Examples 1 and 2 were placed in a glass bottle, and stored for 2 weeks in an open plug state under the conditions of 50° C. 85% RH to give stored products.

Experimental Example 2

The tablets or film-coated tablets (non-stored products) obtained in Production Examples 1 and 2 or stored product obtained in Experimental Example 1 were subjected to a test at 50 rpm according to the Dissolution Test Method (Paddle Method) of the Japanese Pharmacopoeia, 15th Edition, and using diluted McIlvaine buffer to pH 5.0 as a test solution. The test solutions were sampled at 15 min and, where necessary, 10 min after the start of the dissolution test, and the dissolution rates were measured by HPLC method.

The results are shown in the above-mentioned Tables 1-4. From the results, the tablets and film-coated tablets of Examples 1-15 were shown to have good dissolution property.

The results of Table 1 reveal that lactose is particularly preferable as the filler (component (b')) contained in the granulated particles in the embodiment of the tablet (I) of the present invention, which is without addition of a later powder.

The results of Table 2 reveal that lactose, D-mannitol, erythritol and crystalline cellulose have good dissolution property as the filler (component (b)) contained in the granulated particles in the film-coated tablets of the present invention, which accompany addition of a later powder, and that lactose and D-mannitol have better dissolution property and, in consideration of the 10 min value and the like, lactose has still better dissolution property.

The results of Examples 3, 4 in Table 2, Table 3 and Table 4 reveal that the dissolution property was good when either or both of the filler (component (e)) and the cellulose-based disintegrant (component (f)) was/were used as the later powder of the film-coated tablet of the present invention. In addition, it was shown that the fillers (component (e)) of the later powder are more preferably lactose and D-mannitol, and lactose is more preferable in consideration of dissolution 10 min value and the like; the cellulose-based disintegrants (component (f)) of the later powder are more preferably CMC-Ca and L-HPC, and CMC-Ca and L-HPC are more preferably contained in combination in consideration of 10 min value and the like.

The present invention has shown that addition of a later powder prevents degradation of dissolution property even after application of film coating and a film-coated tablet with good dissolution property can be obtained (e.g., Table 3, Examples 7-11, Table 4, Examples 12-15 etc.).

Experimental Example 3

The tablets or film-coated tablets obtained in Production Examples 3-7 were subjected to a test at 50 rpm according to the Dissolution Test Method (Paddle Method) of the Japanese Pharmacopoeia, 15th Edition, and using diluted McIlvaine buffer to pH 5.0 as a test solution. The test solutions were sampled at 15 min and, where necessary, 10 min after the start of the dissolution test, and the dissolution rates were measured by HPLC method.

The results are shown in the above-mentioned Tables 5-10. From the results, the tablets and film-coated tablets of Examples 16-34 were shown to have good dissolution property.

The results of Table 5 reveal that cellulose-based disintegrant is good as the disintegrant (component (c)) to be added to the granulated particles, and CMC-Ca and croscarmellose Na are better as the cellulose-based disintegrants.

The results of Table 6 reveal that cellulose-based disintegrant is good as the disintegrant (component (f)) to be added to the later powder, and CMC-Ca and croscarmellose Na are better as the cellulose-based disintegrants.

The results of Table 7 reveal that granulated particles containing natural starch show good dissolution property.

The results of Table 8 reveal that PVA, HPC-L, HPMC are good, and PVA and HPC-L are better, as the water-soluble binders.

The results of Table 9 reveal that magnesium stearate, calcium stearate and sodium stearyl fumarate are good as the lubricant.

INDUSTRIAL APPLICABILITY

The tablet (tablets (I), (II) and film-coated tablet) of the present invention has good dissolution property, and compound A and a pharmaceutically acceptable salt thereof are useful as beneficial therapeutic agents for diseases such as frequent urination or urine incontinence, and the like. The production method of the present invention is useful since it can produce the tablet of the present invention, which is useful as beneficial therapeutic agents for diseases such as frequent urination or urine incontinence, and the like.

This application is based on U.S. provisional application No. 61/064,012, the contents of which are incorporated in full herein.

The invention claimed is:

1. A tablet free of film coating obtained by mixing granulated particles obtained by granulating a mixture of (a)

(+)-3-{1-[3-(trifluoromethoxy)benzyl]piperidin-4-yl}-4-phenyl-3,4-dihydro-2(1H)-quinazolinone or a pharmaceutically acceptable salt thereof, (b') one or more kinds of fillers selected from lactose and crystalline cellulose, (c) a cellulose-based disintegrant, (d) one or more kinds of water-soluble binders selected from polyvinyl alcohol, hydroxypropylcellulose and hypromellose 2910, and (g) natural starch.

2. The tablet according to claim 1, wherein the filler of the aforementioned (b') is lactose.

3. The tablet according to claim 1, showing good dissolution property.

4. The tablet according to claim 1, further comprising a lubricant.

* * * * *